(12) United States Patent
Neracher (10) Patent No.: US 6,994,127 B2
(45) Date of Patent: Feb. 7, 2006

(54) INJECTION DEVICE WITH RE-USABLE PRESSURE GENERATING MEANS

(75) Inventor: Arnold Neracher, Anieres (CH)

(73) Assignee: Tecpharma Licensing AG, Burgdorf (CH)

( * ) Notice: Subject to any disclaimer, the term of this patent is extended or adjusted under 35 U.S.C. 154(b) by 38 days.

(21) Appl. No.: 10/601,326

(22) Filed: Jun. 20, 2003

(65) Prior Publication Data

US 2004/0055662 A1    Mar. 25, 2004

Related U.S. Application Data

(63) Continuation of application No. PCT/IB01/02525, filed on Dec. 17, 2001.

(30) Foreign Application Priority Data

Dec. 21, 2000 (EP) ................................ 00128096

(51) Int. Cl.
*B65D 1/04* (2006.01)

(52) U.S. Cl. ..................... 141/27; 141/21; 141/24; 604/70

(58) Field of Classification Search ............ 141/21–28; 604/68, 70

See application file for complete search history.

(56) References Cited

U.S. PATENT DOCUMENTS

| 2,650,591 | A | | 9/1953 | Love |
| 2,687,725 | A | | 8/1954 | Hein, Jr. |
| 2,798,486 | A | | 7/1957 | Hein, Jr. |
| 6,203,521 | B1 | * | 3/2001 | Menne et al. .................. 604/68 |
| 6,440,099 | B2 | * | 8/2002 | Haar et al. ..................... 604/68 |

FOREIGN PATENT DOCUMENTS

EP    0 853 952 A1    7/1998

* cited by examiner

*Primary Examiner*—Timothy L. Maust
(74) *Attorney, Agent, or Firm*—Dorsey & Whitney LLP

(57) ABSTRACT

An injection device having a propulsion system comprises a container, a re-usable pressure generating mechanism and a source of potential energy for propelling a fluid with sufficient pressure through an orifice to create a jet enabling subcutaneous or intracutaneous delivery of the fluid, the source of potential energy primarily in the form of a compressible substance that is put under pressure within the container by the pressure generating mechanism, whereby said potential energy is substantially compression energy of said substance, wherein said substance is liquid, solid, or other non-gaseous substance as defined at ambient temperature and said pressure.

24 Claims, 7 Drawing Sheets

INJECTION DEVICE WITH RE-USABLE PRESSURE GENERATING MEANS

CROSS-REFERENCE TO RELATED APPLICATION(S)

This application is a continuation of International Application No. PCT/IB01/02525, filed on Dec. 17, 2001, which claims priority to European application 00128096.5, filed on Dec. 21, 2000, the contents of both are incorporated herein by reference. The international application was published under PCT Article 21(2) in English.

BACKGROUND OF THE INVENTION

The present invention relates to a propulsion device with reusable pressure generating means, in particular for generating a liquid micro-jet for transdermal injection.

Manually operated syringes with needles are the most common form of hypodermic injection devices. They have the advantage of being reliable and low cost. The disadvantages are, inter alia, the risk of transmitting diseases by re-use of the syringe, and the pain felt by the patient.

In view of these disadvantages, there have been many attempts to provide needleless hypodermic injection devices in which a liquid to be injected is propelled at high speed by a pressure generator, thereby piercing the skin of a human or animal patient. Such devices are, for example, described in patent publications U.S. Pat. Nos. 3,537,212, 2,687,725, 4,596,556, 4,722,728, 4,874,367, 4,966,581, 5,501,666 and WO 98/41250. In order to ensure sterility and avoid contamination of medicaments to be injected, certain conventional devices as described in patents U.S. Pat. No. 4,874,367 and U.S. Pat. No. 4,966,581 comprise re-usable pressure generating mechanisms receiving disposable cartridges containing the liquid to be injected. The devices described in these patents are very complex and made of a large number of pieces. They are also bulky, costly and limited in their performance, particularly as concerns the injection pressure and jet diameter which are in the order of 70 bars or less and 100 to 330 $\mu$m, respectively, although initial peak pressure may attain around 300 bars. Insufficient pressure and a large diameter jet increases pain and the risk that only a portion of the medicament is injected, especially with respect to patients having a resistant skin. Moreover, the depth of administration of liquid is difficult to control accurately with conventional devices.

Considering the abovementioned disadvantages, an object of the present invention is to provide a re-usable propulsion device that is effective, reliable and compact. It is advantageous to provide a propulsion device for needleless transdermal administration of liquids. It is advantageous to provide an injection device that is safe to operate. It is advantageous to provide an injection device that eliminates the risk of disease transmission by re-use. It is advantageous to provide an injection device that is painless to use. It is advantageous to provide a propulsion system that enables the dosage to be varied. It is advantageous to provide a hypodermic injection device that is easy to use and cost effective.

SUMMARY OF THE INVENTION

Objects of the invention have been achieved by providing the injection device according to claim 1.

Disclosed herein is an injection device having a propulsion system comprising a container, a re-usable pressure generating mechanism and a primary source of potential energy for propelling a liquid with sufficient pressure through an orifice to create a jet enabling transdermal delivery of the liquid, the primary source of potential energy primarily being in the form of a compressible substance that is put under pressure within the container by the pressure generating mechanism, whereby said potential energy is compression energy of said substance, wherein said compressible substance is a liquid, solid or other nongaseous substance, as defined at ambient temperature and pressure.

The compressible substance may, for example, be a soft matter or other visco-elastic substance, such as a substance belonging to the family of polysiloxanes, which is not expensive and has a large elastic compression range. Certain polysiloxanes may be compressed up to 2000 bars with a 15% volume reduction. Polysiloxanes comprise a volumetric compressibility (dV/V) which is in the range of two to four times greater than the volumetric compressibility of water.

In view of the very high pressure and small orifice diameter, it is possible to produce a very fine liquid jet of supersonic speed. Moreover, the injection time may be spread over a few seconds in view of the small jet diameter (e.g. 30–60 $\mu$m) thereby reducing or eliminating pain by giving more time for the medicament to diffuse in the surrounding tissue.

The provision of a compressed liquid or solid as a source of potential energy for propelling a liquid to be injected is very advantageous over prior art systems using mechanical energy sources such as springs, or compressed gas. The use of springs, for example, requires large dimensions to obtain the required propulsion energy to ensure that a patient's skin is pierced, and even then the liquid jet diameter is typically in the range of 200 $\mu$m in order to ensure sufficient power of the jet. Prior systems using compressed gas, as defined at ambient temperature and pressure, are limited by the maximum pressure of the gas until a change of state to the liquid form, which defines the maximum pressure of the propulsion system. For example, carbon dioxide liquefies at approximately 70 bars and nitrogen protoxide at 75 bars, these gases being the most frequently considered for use in conventional propulsion systems. The large volume change of a compressed gas is also a safety concern, since in the event of rupture of the gas container, loose particles of the device are driven by the large expansion of gas liberated from the container.

Preferred compressible substances used in the invention, such as polysiloxane oils or gels, or vulcanised silicon rubber, which may be compressed for example to 2000 bars to obtain up to 15% volume reduction, do not cause an explosion in th event of rupture. Furthermore, a liquid or solid compressible substance can be compressed in a container at much higher pressure since there is no change of state and the substance escapes less easily through the sealing joints than gaseous substances. Vulcanized silicon rubber or high molecular weight polysiloxane oils, for example, which are very viscous, are much easier to contain without leakage through seals compared to gas and even liquids with low viscosity such as water. While polysiloxane oils or gels are preferred substances in view of the combination of high viscosity, relatively high compressibility and low cost, numerous other substances with compressibility greater than water and preferably greater than double the compressibility of water could be implemented in certain embodiments of the invention. Examples of other compressible substances that may be implemented in the present invention are cork, polyurethane and butyl polymers. These substances have volumetric compressibility ratios (dV/V) in the range 1.2 to 2 times that of water.

The high energy density that may be stored in compressible substances according to this invention enables the hypodermic injection device to be compact and low cost.

The propulsion system may further comprise a secondary source of potential energy generating a lower pressure than the primary source. This enables the injection depth to be accurately controlled, in particular to limit the depth of liquid delivery once the skin has been pierced by the initial high pressure jet. This is important for example in applications requiring intradermal or subcutaneous delivery. The secondary source of potential energy may be in the form of a metal spring, a paired of opposed permanent magnets, a gaseous substance, or other elastic member mounted in the propulsion system container.

In certain embodiments, disposable cartridges or ampoules containing the liquid to be injected are mounted in the container by the user. This enables the ampoules to be manufactured, stored and used with the required sterility and accuracy of dosage. This also enables flexibility in the packaging and dosage of the liquid to be injected which can be determined by the volume in the ampoule.

The single use ampoule may further contain the compressible substance for assembly in the container, or the compressible substance could be provided in the container and re-used.

In some embodiments, the compressible substance may be put under pressure in a rear chamber of the container separated from a front chamber by a wall provided with a valve to actuate the device. When the valve is opened, the compressible substance flows into the front chamber and drives a piston that propels the liquid to be injected.

In other embodiments, both the compressible substance and the liquid to be injected are put under pressure in the container, the pressure being maintained by blocking the nozzle orifice with a removable plug or a valve that may be actuated.

In view of the high pressures that may be attained by the present invention, and therefore the high speed of the liquid jet produced, the jet may pierce the skin of a patient without the need for a needle in an effective, reliable and painless manner.

In the embodiments where a plug blocks the nozzle orifice, the plug may be of a material that may be decomposed by external means such as heat or ultrasound, for example a wax or paraffin plug that may be removed by locally heating the injection device. The plug may also be a mechanical member such as steel wire retractable from the orifice. The floating piston or deformable wall moves once the orifice is unblocked due to the drop in pressure in the capsule portion comprising the liquid to be injected. A valve, for example a rotatable valve provided with a passage therethrough that interconnects the liquid container portion with the outlet nozzle orifice in an actuated position, and blocks the outlet of the liquid container portion in a closed position, may also be implemented.

In another embodiment, the portion of the single-use capsule containing the liquid to be injected is surrounded by a deformable wall arranged inside a portion of the capsule containing the compressible substance, and the retaining means comprise a plug closing the orifice of the nozzle portion. Once the retaining means are removed, the deformable wall of the container portion containing the liquid to be injected is crushed under the pressure of the compressible substance.

The container may be made of metal, for example made of stainless steel, which may be provided with a precious metal layer on its inside surface (for example gold, platinum, palladium) or with a polymer such as Teflon. The inside layer facilitates sliding of the piston and improves sealing. It should be noted that polysiloxane oils are very advantageous with respect to a gas, on the one hand, due to their viscosity which may be very high depending on the molecular weight of the oil, thereby reducing the demands on sealing, and on the other hand, a large portion of the stored compression energy may be transformed into work.

The nozzle portion may comprise a separate member mounted in or to the capsule container, or may be integrally formed with the wall of the capsule container.

The orifice of the nozzle portion may have a diameter in the order of 10 to 150 microns, at least over a defined length, such that the liquid jet remains coherent for a few millimetres after exiting the nozzle. If the displacement of the piston between the beginning and end of the injection corresponds to a variation in volume of the compressible substance of 7.5%, this corresponds to a pressure variation of 1000 bars for monomer hexamethylsiloxane. A pressure of this order combined with a very fine nozzle orifice enables the production of a supersonic jet for liquid injections through skin in an extremely reliable and painless manner. Moreover, the supersonic shock wave causes degradation of the jet in droplets a few millimeters from the nozzle, thereby increasing the safety of the device. The jet could of course also be produced at subsonic speeds depending on the injection needs and requirements.

The compressible substance may be compressed by displacing a piston in the container, thereby reducing the volume occupied by the compressible substance. The piston of the pressure generating mechanism may be displaced by a threaded member with a fine pitch engaging in a complementary thread at a rear end of the container portion. The pressure generating mechanism may comprise a motor coupled to the piston, for example via a threaded member, to drive the piston. The motor may be connected to and controlled by an electronic control system. A valve that opens and closes the outlet nozzle orifice may be actuated by a valve actuator, which may also be controlled by the electronic control system.

The injection device may further comprise a liquid supply system comprising a container holding a multi-dose reserve of liquid to be injected, for supplying the propulsion system. The liquid supply container may be connected to the liquid container portion of the propulsion system via the valve. The liquid supply system may comprise a motorised feed mechanism controlled by the electronic control system to regulate, inter alia, the volume of liquid supplied to the propulsion system.

Further objects and advantageous aspects of the invention will be apparent from the following description, claims and accompanying drawings.

BRIEF DESCRIPTION OF THE DRAWINGS

FIG. 3b is a longitudinal section of the single-use capsule of the embodiment of FIG. 3a;

FIG. 3c is a longitudinal section of the container and pressure generating mechanism of the propulsion unit of the embodiment of FIG. 3a;

DETAILED DESCRIPTION OF THE INVENTION

Figures 1A, 1B:
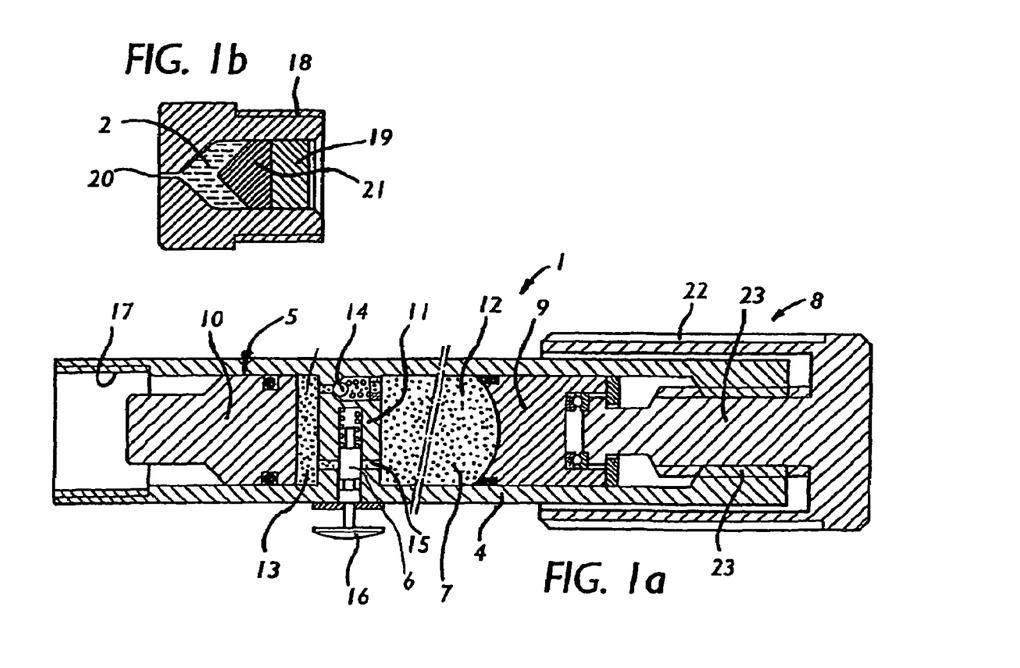
FIG. 1a is a longitudinal section of a re-usable propulsion unit of an injection device according to this invention, for use with single-use capsules.
FIG. 1b is a longitudinal section of a capsule for assembly to the propulsion unit of FIG. 1.

Referring to FIGS. 1a and 1b, an injection device comprises a propulsion system 1 and a disposable capsule 3 mountable thereto, for the administration of a liquid 2 contained in the capsule under the skin of a human or animal patient.

The propulsion system comprises a container 4, a pressure transmitting member 5 in the form of a piston 10, a pressure retaining means 6, a pressure generating means 8, and a compressible substance 7. The compressible substance 7 under pressure is a primary source of potential energy for propelling the liquid to be injected.

The compressible substance may advantageously comprise a polysiloxane oil which has the ability to store a large amount of potential energy through elastic molecular compression, for example up to 100 times more energy than a conventional metal spring occupying the same volume. The molecules of polysiloxanes behave as three-dimensional springs, and the stored energy is equal to the sum of the molecular cohesion energy of about $4-10^{-21}$ joules per molecule which corresponds to the thermal energy $K_BT$ at 20° C., where $K_B$ is Boltzmans constant, and T is temperature in Kelvin. The elastic property of polysiloxanes is particularly advantageous to the present invention since it allows the injection device to be compact, cost-effective, and comprise few components. Depending on the molecular weight, polysiloxanes typically have volumetric compressibility values (dV/V at a given pressure) three to four times greater that the volumetric compressibility of water. While polysiloxanes are a preferred soft matter for use in the present invention, other soft matter substances may also be used. The properties of soft matter are known and described, for example, in the reference "Review of Modern Physics", Nobel Lecture in Physics, vol. 64, p. 645.

Polysiloxane oils are limpid, clear, odourless, insipid, visco-elastic liquids resistant to high and low temperature and which are low-cost. They are neither toxic nor dangerous from the physiological point of view and may be used in dermatological and cosmetic applications. Polysiloxane oils have a low viscosity variation as a function of pressure which advantageously facilitates fluid exchange, but they have a high surface tension such that they are non-miscible with water solutions. Polysiloxane oils also have lubricating properties between metals and polymers and rubber, which advantageously facilitates sliding between mobile members.

The family of polysiloxane oils comprises, inter alia, the following substances:
polymethylhydrogensiloxane
polydimethylsiloxane
polytrimethylsiloxane
hexamethylcyclotrisiloxane
decamethyltetrasiloxane
hexamethyldisiloxane (H 7310-Witheco)
octamethyltrisiloxan (O 9816-Witheco)
alpha, beta, gamma, and theta gels from Geltec Corporation.

An advantageous property of polysiloxane oils is the reduction of viscosity with shear velocity which enables rapid flow of such oils through small orifices. Polysiloxane oils may have viscosities ranging from 0.6 to $10^7$ centistokes depending on molecular weight. This property enables the oil to be chosen according to the requirements of the embodiment, in particular embodiments that require flow of the compressible substance through passages of small cross sections, as is the case for the embodiment shown in FIG. 1. The other embodiments may be provided with a compressible substance in the form of an elastic solid, such as vulcanised silicon rubber, for example of the type SilGel® 6/2 manufactured by Wacker-Chemie, having volumetric compressibility only about 25% lower than low viscosity polysiloxanes.

As an example, monomer hexamethylsiloxane $(CH_3)_6SiO$ may be elastically compressed under a pressure of approximately 2000 bars with a volume reduction of about 15%. If the volume of the liquid to be injected is 0.1 ml, and the minimum pressure at the end of injection is chosen to be 1000 bars, the non-compressed volume of polysiloxane is 1.3 ml. The device according to the invention is not only extremely compact, but enables the injection of liquid at pressures well above those available in conventional systems, which makes possible the production of a very fine jet that can surpass supersonic speed. Very reliable and safe hypodermic injection can thus be effected with the present invention.

For example, at 1000 bars pressure, the liquid to be injected can be propelled through nozzle orifices having diameters around 30–60 µm with sufficient speed to pierce a patients skin, and whereby injection time is slow enough to enable the injected liquid to diffuse in the surrounding tissue thus reducing injection pain. In conventional devices, the nozzle orifice must have a much larger diameter in view of the lower injection pressure, with the consequence that injection time is reduced and the injected liquid collects locally in the patient's tissue thus causing pain.

Moreover, the injection device according to the invention comprises very few parts which leads to low-cost production, in addition to simple and reliable use.

Referring to FIGS. 1a and 1b, the pressure generating means comprises a piston closing a rear end of the container 4. The piston 10 closes a front end of the container portion 4. A separating wall 11, forming part of the pressure retaining means 6, is provided inside the container portion 4 between the rear piston 9 and front piston 10. A large volume chamber 12 is formed between separating wall 11 and the rear piston, and a small volume chamber 13 is formed between the separating wall and the front piston. The separating wall is provided with a return valve 14 to allow compressible substance 7 from the front chamber to flow into the rear chamber, whereby flow in the opposite direction is prevented. An actuation valve 15 is provided to allow the compressible substance to flow from the rear chamber 12 to the front chamber 13 upon actuation of the valve, for example when the user presses a button 16 thereof.

The front end of the container is provided with a threaded portion 17 for releasably mounting a capsule 3 containing the liquid to be injected, the capsule being provided with a complementary threaded portion 18. Other releasable fixing means could however be provided, such as a bayonet type connection or releasable spring latches.hAsrear end of the capsule is sealingly closed by a piston 19 that is driven by the propulsion system piston 10 on actuation of the device thereby propulsing the liquid 2 through the nozzle orifice 20. The capsule piston 19 may be provided at its front end with a cone shaped elastic member 21 in order to ensure that substantially all the liquid to be injected is propelled out of the capsule.

The pressure generating mechanism 8 is mounted to the rear end of a container and comprises a grip portion 22 and a ram portion 23 in the form of a threaded bolt engaging a complementary threaded portion 24 of the container portion. As the mechanism 8 is screwed and the ram portion 23 is threaded into the container, the piston 9 is displaced and compresses the compressible substance 7. The amount of turns applied to the grip 22 determines the pressure of the compressible substance 7 which can thus be adjusted according to the application. To actuate the device, the user opens the actuation valve 15 by depressing the button 16 such that the compressible substance in the rear chamber 12 flows to the front chamber 13 and drives the piston 10 which drives the capsule piston 19. After use, the capsule 3 is removed from the propulsion unit and the pressure generating element 8 is unwound, thereby aspirating the compressible substance 7 through the return valve 14 back into the rear chamber 12. A new capsule 3 may then be fitted into the front end of the container. It is advantageous in this embodiment to have a compressible substance of low viscosity, such as a low molecular weight polysiloxane, such that the flow resistance through the valves 15 respectively 14 is low.

Figure 2A:
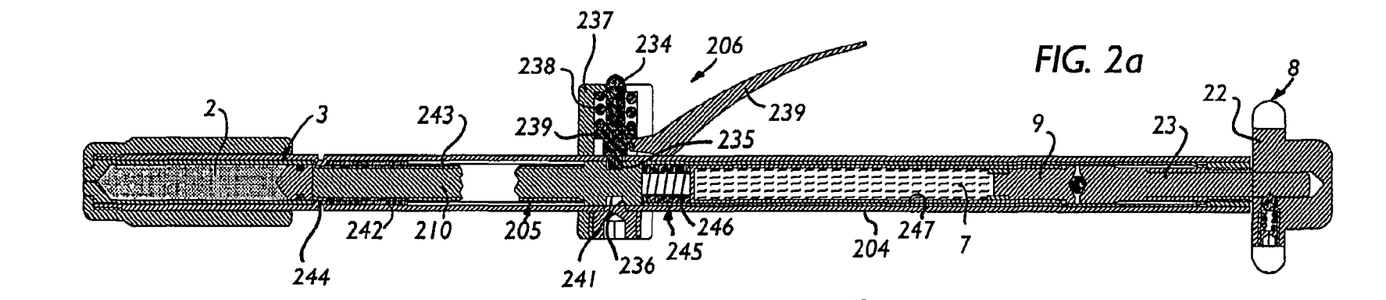
FIG. 2a is a longitudinal section of a re-usable injection device according to another embodiment of this invention, with a two-stage propulsion unit in a compressed state.
Figure 2B:
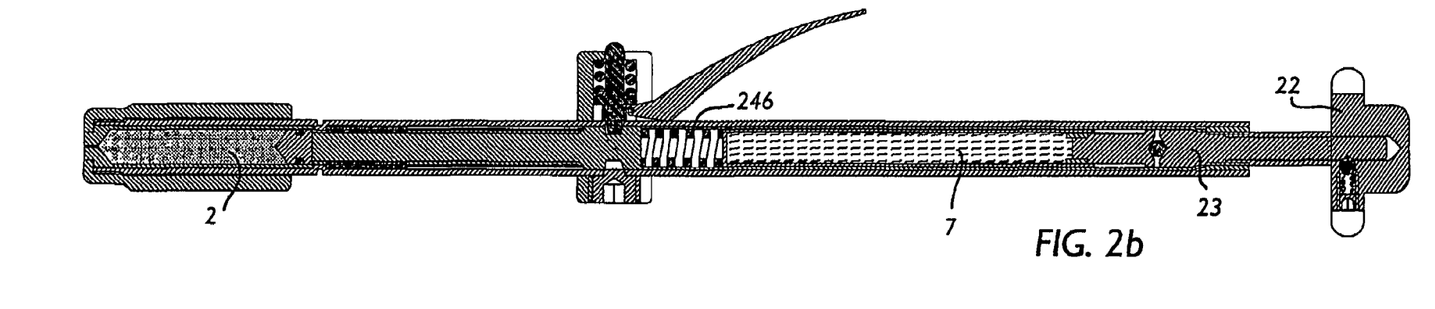
FIG. 2b is a view similar to FIG. 2a, except that the propulsion unit of the device is in an uncompressed state.
Figure 2C:
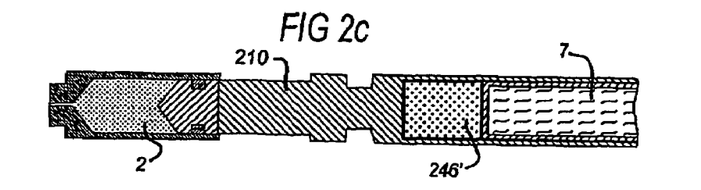
FIGS. 2c to 2e are partial longditudinal sections of variants of a two-stage propulsion unit that may be implemented in devices according to this invention.
Figure 2D:
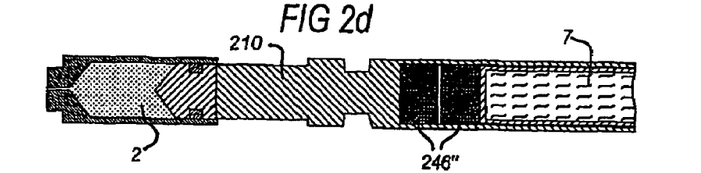
Figure 2E:
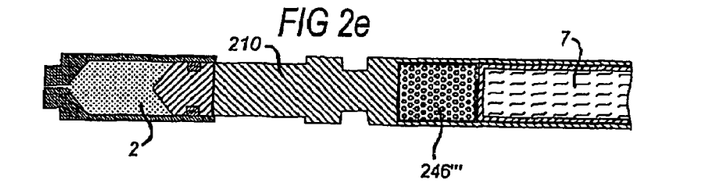

Referring to FIGS. 2a and 2b, a second embodiment of an injection device will now be described. In order to avoid repetition, the features of this embodiment that are similar to the embodiment of FIGS. 1a and 1b will be designated with the same reference numbers, and their function can be understood by referring to the above description of the first embodiment.

In the second embodiment, the pressure retaining means 206 is in the form of a releasable trigger mechanism engaging the front piston 210 to hold it in the loaded position shown in FIG. 2a. The trigger mechanism comprises a moveable stop pin 234 provided with an abutment shoulder 235 near a free end of the pin, engaging against a complementary abutment shoulder 236 provided on the piston 210. The abutment shoulders are inclined at a slight angle with respect to the plane perpendicular to the longditudinal axis A of the propulsion system in order to reduce the force required to disengage the stop pin from the piston, especially considering the very high pressure that can be generated in the compressible substance 7. The optimal inclination angle, which is preferably in the range of 2° to 10°, depends however on a number of factors such as the coefficient of friction between the materials forming the abutment shoulders, the contact geometry and surface area, and the maximum force applied on the piston when the propulsion system is loaded. The pin 234 is guided in a housing portion 237 mounted on the container and is pressed towards the piston 210 by a spring 238 engaging a flange 239 of the pin. The flange also serves as a shoulder to enable an actuation lever 240 engaging thereunder to lift the pin and disengage it from the piston 210. The main function of the spring 238 is to bias the pin into the piston indent 241 when the piston is retracted and a new capsule 3 is mounted in the propulsion unit.

The dosage of liquid 2 to be injected can be adjusted by varying the travel of the propulsion unit piston 210. This is achieved in the present embodiment by providing a threaded position adjustment ring 242 mounted on a threaded portion 243 of the piston 210, that abuts against an annular stop 244 provided on the inside of the container 204 at the end of the injection. The displacement of the piston, and therefore the volume of liquid to be injected, is decreased by threading the ring 242 towards the stop 244.

Figure 2F:
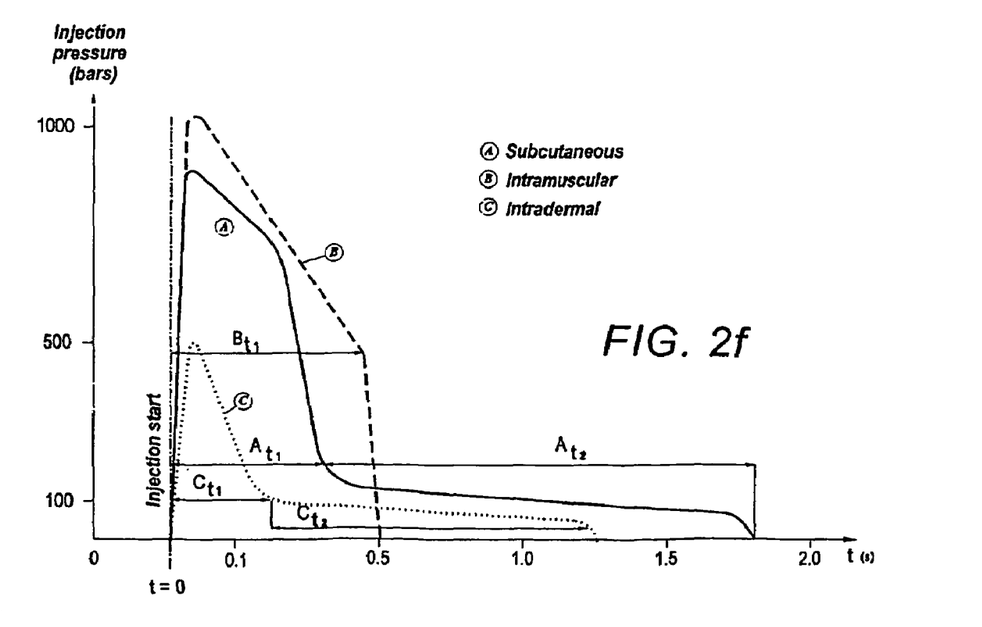
FIG. 2f is a graph illustrating different injection pressure curves over time during actuation of one-stage and two-stage injection devices according to the invention.
Figure 3A:
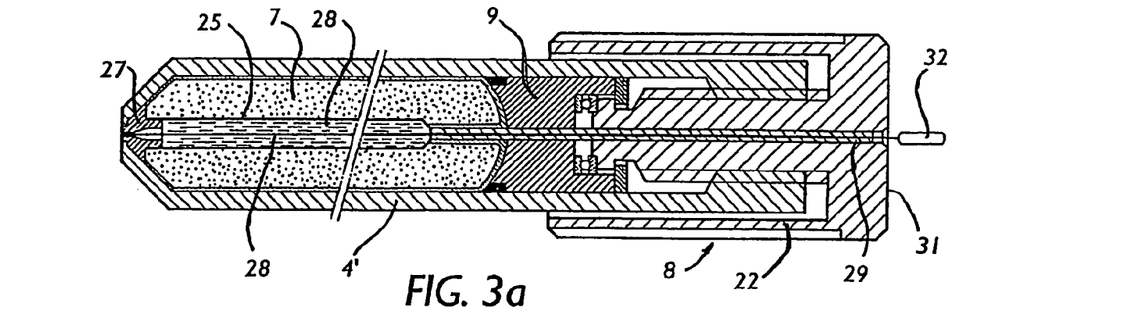
FIG. 3a is a longitudinal section of a second embodiment of an injection device according to this invention, with a single-use capsule containing the compressible substance and the liquid to be injected mountable in a container of the propulsion unit.
Figure 3B:
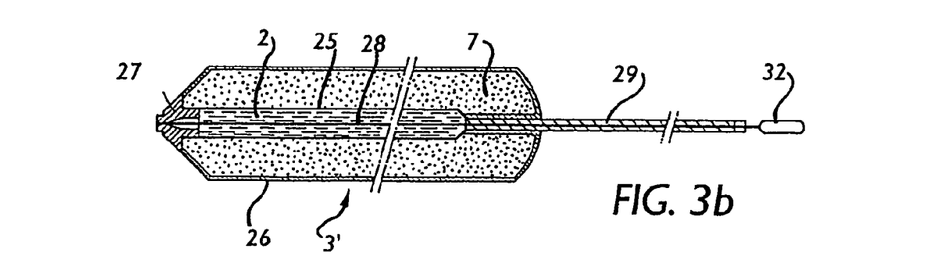
Figure 3C:
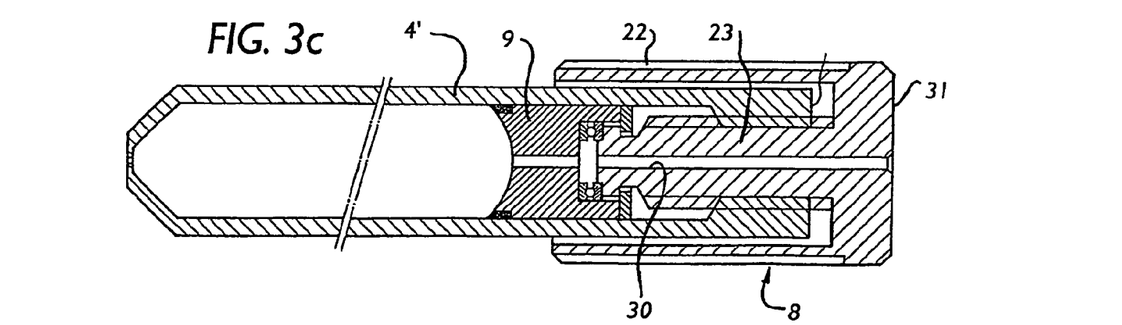
Figure 4:
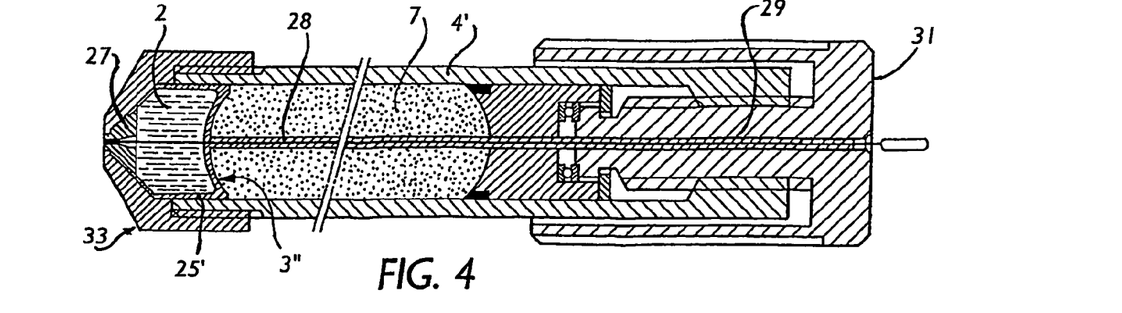
FIG. 4 is a longitudinal section of a variant of the embodiment of FIG. 3a, in which the compressible substance is permanently mounted in the propulsion unit rather than to the single-use capsule.

In addition to the primary source of potential energy provided by the compressible substance 7, the propulsion system of the second embodiment comprises a secondary source of potential energy 245 that generates a lower pressure P2 than the maximum pressure P1 generated by the primary potential energy source, as illustrated in FIG. 2f. The compressed substance 7 liberates energy in an initial phase of high pressure injection, peaking for example at around 800 to 1000 bars, followed by liberation of pressure from the secondary source at relatively low pressure, for example 70 bars and less. This double injection pressure stage is very advantageous since it enables the injection depth to be accurately controlled, for example to deliver liquids such as insulin or other medicines intradermally or subcutaneously. The initial high pressure enables a very fine supersonic liquid jet to be formed to pierce skin, followed by the lower pressure second stage jet to deliver the liquid at a controlled depth below the outer surface of the skin, avoiding excessive penetration that would ensue if the initial high pressure were maintained over a longer period. Furthermore, the volume of liquid to be injected can be increased with the low pressure secondary energy source, since it has a larger compression ratio than the compressible substance 7.

The double stage propulsion system advantageously enables the desired depth of injection and the volume of injected liquid to be reliably performed by an appropriate selection and design of the primary and secondary potential energy sources, and in particular by adjusting the relative stored energy of each source. Depending on the contribution of the primary energy source relative to the secondary energy source, different injection pressure characteristics over time can be obtained as illustrated in FIG. 2f.

Curve B represents the pressure characteristic of a propulsion system adapted to deliver liquid intramuscularly. In this case, since the injection depth is large, the propulsion system may be provided with only the primary energy source of compressed liquid or solid substance. In the present example, initial injection pressure is 1000 bars, and decreases to 500 bars at the end of injection over an injection time $Bt_1$ of about 0.5 seconds. For a given volume of liquid to be injected, the pressure decrease and injection time, in other words the slope of curve B, can be varied by changing the volume of compressed substance and the nozzle orifice diameter. If a large volume of liquid is to be injected, it may however be advantageous to also have the secondary potential energy source.

Curve A represents for example the pressure characteristic of a propulsion system adapted to deliver liquid subcutaneously whereas curve C represents the pressure characteristic of a propulsion system adapted to deliver liquid intradermally. In these cases the propulsion system comprises both the primary energy source and the secondary energy source, but the stored energy of the primary energy source relative to that of the secondary energy source in a propulsion system corresponding to curve A is greater than for a propulsion system corresponding to curve C. The relative stored energy of the respective energy sources can be easily adjusted by varying the volume of compressible substance 7, a larger volume corresponding to more stored energy.

The step at injection time $At_1$ in curve A is achieved by providing a stop in the propulsion system container to stop, after a specified volume increase (pressure decrease), the piston or container portion separating the compressible substance from the secondary source of potential energy, such that the secondary energy source then takes over to complete injection. In a propulsion system corresponding to curve C, no stop for the primary energy source is provided, the secondary energy source taking over from the primary energy source approximately at time $Ct_1$ when the pressure of the compressible substance drops to the pressure exerted by the secondary energy source.

The secondary energy source may comprise: a spring, for example a metal coil spring 246, as shown in FIGS. 2*a* and 2*b*; a gas 246' as shown in FIG. 2*c*; a pair of opposed permanent magnets 246", for example FeNd permanent magnets, as shown in FIG. 2*d*; or an elastic substance comprising gas-filled micro-capsules 246'", as illustrated in FIG. 2*e*, mounted between the piston 210 and the compressible substance 7. The secondary energy source could also be mounted at the rear end of the propulsion device, for example between the rear piston 9 and the compressible substance 7 or between the ram portion 23 and the rear piston 9. The compressible substance 7 may be enclosed in an inner container portion 247 slidably mounted in the container 204, to provide a separation from the secondary energy source.

The secondary energy source may also be directly integrated with the primary energy source, for example as a gas dissolved in the compressible substance or encapsulated in cavities or pores in the compressible substance.

Referring to FIGS. 3*a* and 3*b*, another embodiment of an injection device is shown with a pressure generating mechanism 8 which may be similar to the one described in relation to FIG. 1, mounted to a reusable container 4' for receiving a capsule 3' comprising the liquid to be injected 2 in a flexible membrane 25 surrounded (at least partially) by the compressible substance 7 in a membrane 26. If the compressible substance is silicon rubber or other compressible solid rather than a liquid polysiloxane, the membrane 26 is not necessary. The capsule further comprises a nozzle portion 27 with an outlet orifice blocked by a plug in the form of a high tensile strength wire 28. The wire extends rearwardly through the membrane 25 into a long tail portion 29. The tail portion is received in a central passage 30 in the pressure generating mechanism extending through to the rear end 31 thereof such that the end 32 of the tail portion is accessible. The tail portion 29 may for example be made of plastic surrounding or encapsulating the wire 28. As the wire is very fine, for example around 50 $\mu$m diameter, the frictional force retaining it is quite low and very easily overcome by a user pulling on the end 32 to actuate the device by liberating the nozzle orifice when the compressible substance is under operational pressure.

The container portion 4' can be made in two separable sections (not represented), or have a removable front end cap (similar to the embodiment of FIG. 4) in order to mount the capsule 3' therein. To apply pressure, the pressure generating mechanism is screwed inwardly after assembly of a new capsule.

Referring to FIG. 4, a variant of the embodiment of FIG. 3*a* is shown, in which the compressible substance 7 is mounted and remains in the container portion 4" whereas the single-use capsule 3" is removably inserted in the front end of the device which is provided with a removable cap 33 that is screwed or assembled by other means to the container.

The capsule 3" is provided with a wire 28 plugging the orifice of the nozzle portion 27 and extends in a tail portion 29 beyond a rear end 31 of the injection device in a similar manner to the embodiment of FIG. 3*a*.

The capsule or ampoule membrane 25' is made, for example, of a plastic material, coated as appropriate for the pharmaceutical products contained therein. The nozzle portion 27 may be provided with a metal nozzle tip embedded in a plastic body, the tip being provided with an outlet orifice formed by a ductile insert crimped around the wire plug. The nozzle orifice may also be formed by overmoulding the nozzle portion 27 over the plug portion of the wire 28. The nozzle orifice may have a diameter as small as 5 to 100 microns, but is for most applications preferably in the range of 20 to 50 microns. The nozzle orifice extends over a length which is preferably between about two to five times the diameter of the orifice. The ratio between the orifice length and the diameter enables the production of a liquid jet that remains coherent over a distance sufficient to ensure reliable hypodermic injection, but which destabilizes after a few millimetres, thereby making the jet harmless. In other words, the ratio between the length and diameter of the orifice enables the coherence of the jet to be regulated, such that it is sufficiently coherent for effective and reliable hypodermic injection without being too coherent for safety reasons.

Referring to FIGS. 5*a*, 5*b* and 5*c*, another embodiment of an injection device for propelling a liquid 2, comprises comprises a propulsion system 501 and a liquid supply system 503. The injection device is in particular adapted for the administration of the liquid 2, which may for example be a liquid medicine, through the skin of a human or animal patient.

The propulsion system comprises a container 504, a pressure transmitting member in the form of a flexible membrane 525 enclosing a liquid container portion 560, a pressure retaining means in the form of a rotatable valve 551, a pressure generating means 508, and a compressible substance 7 as described in relation to the aforementioned embodiments. The compressible substance 7 under pressure is, as described in relation to previous embodiments, a primary source of potential energy for propelling the liquid to be injected. Although not shown, the propulsion system may further comprise a secondary potential energy source as described in relation to FIGS. 2*a* to 2*f*, for example mounted between the rear piston 509 and the ram portion 523 of the pressure generating means 508.

The pressure generating means comprises a motor 549 interconnected to an electronic control system 550 that commands and controls the motor. The motor is coupled to the ram portion 523 via a step-down gear mechanism (not shown) to increase the torque that may be applied to turn the ram portion. As in above-described embodiments, the ram portion threadably engages the container portion 504 and drives the rear piston 509 to compress the compressible substance 7.

Figure 5A:
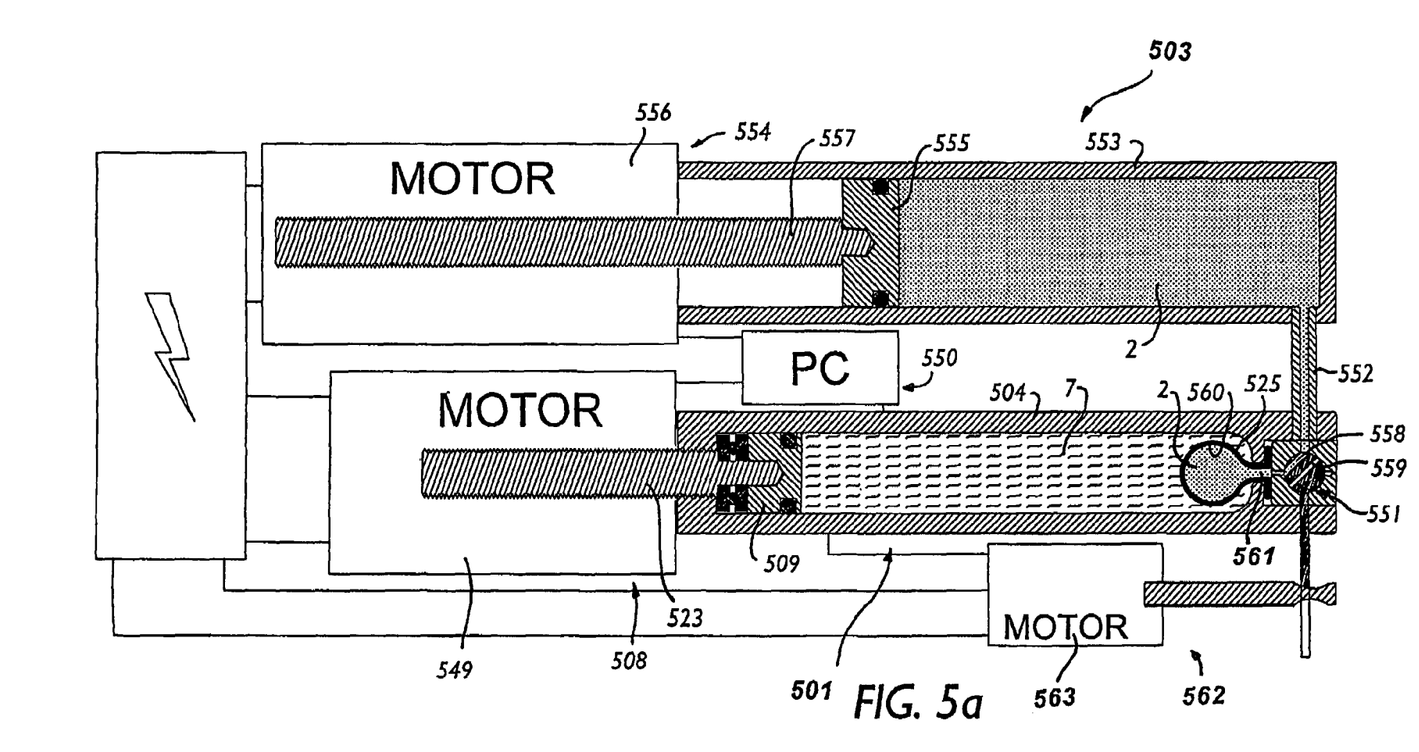
FIG. 5a is a longditudinal section of another embodiment of an electronically controlled injection device with a reusable propulsion unit according to this invention, in a liquid filling phase.
Figure 5B:
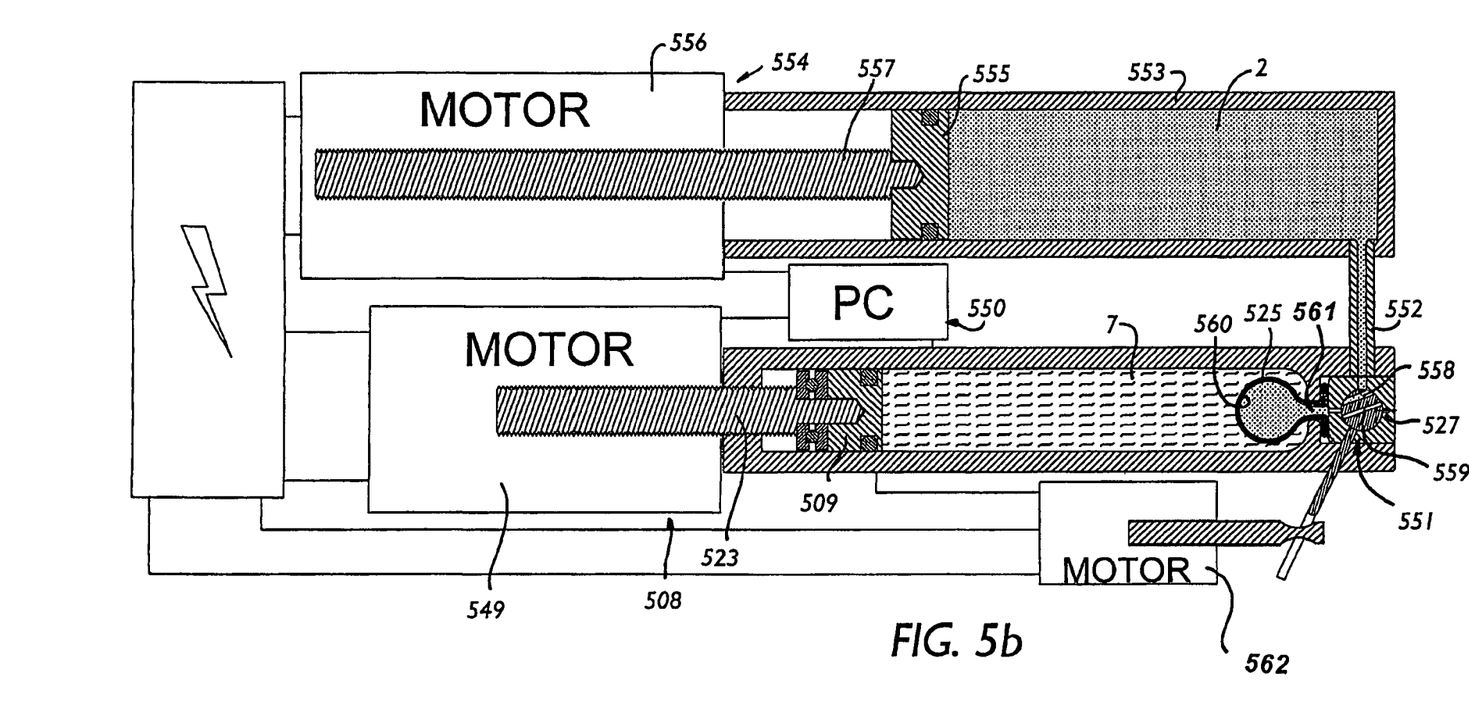
FIGS. 5b and 5c are views similar to FIG. 9a of the device in a loaded, respectively actuated state.
Figure 5C:
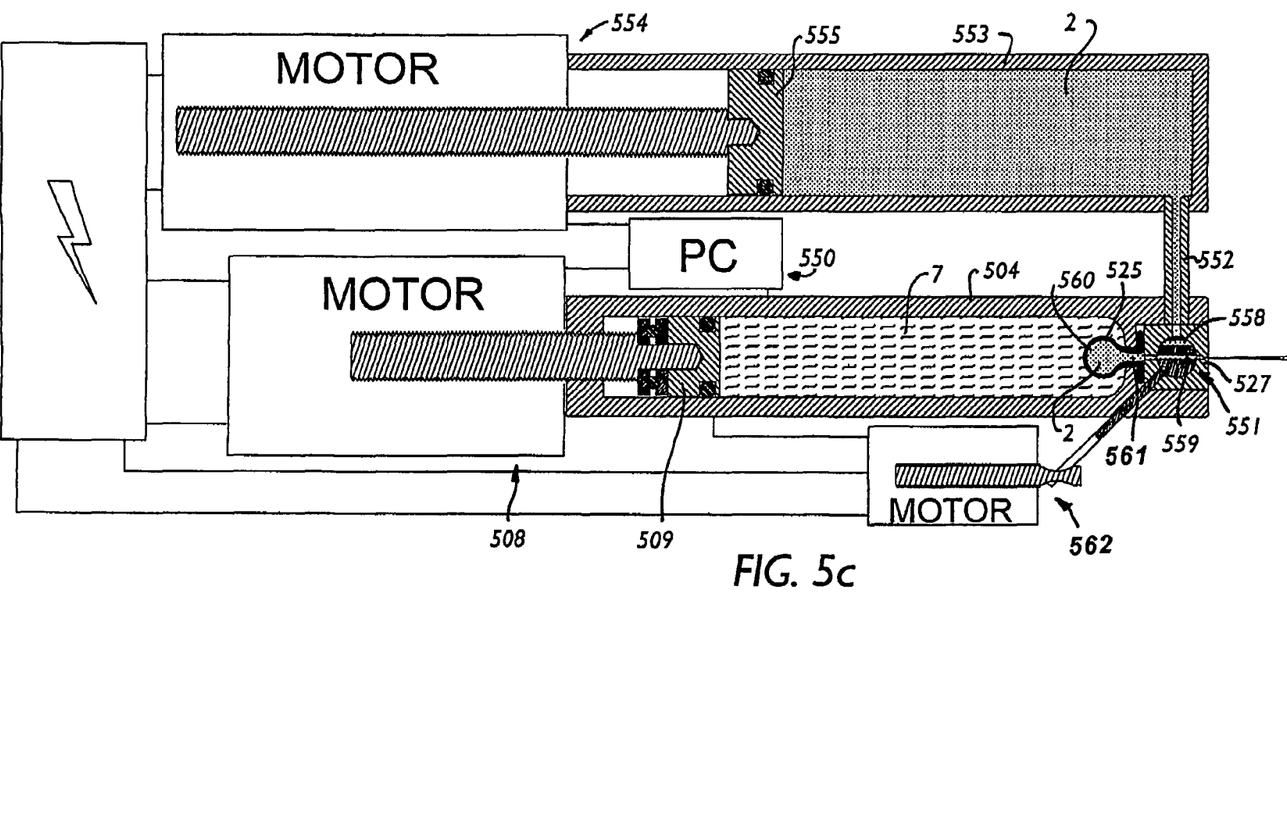

The liquid to be injected 2 is separated from the compressible substance by the flexible membrane 525 mounted at a front end of the container 504 and having an outlet 561. The liquid container portion outlet 561 communicates through a valve 551 with an orifice of a nozzle portion 527 for creating a micro-jet in an actuated position as shown in FIG. 5c, or with a liquid supply conduit 552 communicating with a liquid supply container or reservoir 553 of the liquid supply means, in a refilling position as shown in FIG. 5a, depending on the position of the valve 551. The valve 551 also has a closed position blocking the outlet 561 as shown in FIG. 5b, to enable pressure to be generated in the compressible substance 7 prior to actuation. The valve may be actuated from one position to another by an actuator mechanism 562 comprising a motor 563 coupled to the valve 551 and controlled by the electronic control system 550.

The liquid supply system comprises a feed mechanism 554 for feeding liquid from the liquid supply container 553 to the liquid container portion 560. The feed mechanism comprises a piston 555 driven by a motor 556, for example via a geared down drive arm 557. The motor 556 may be controlled by the electronic control system 550 that also controls the pressure generating mechanism and the valve so that their operation may be coordinated.

The valve 551 may advantageously have a rotatable cylindrical portion provided with a first passage 558 for interconnecting the liquid supply conduit 552 with the liquid container portion outlet 561 in the refilling position of the valve, and a second passage 559 for interconnecting the liquid container portion 560 of the propulsion unit with the outlet nozzle orifice in the actuated position of the valve.

To operate the injection device, a user may for example press a 'load' button or other interface device connected to the electronic control system 550 that commands the valve actuator 562 to rotate the valve into the refilling position shown in FIG. 5a. The liquid supply piston 555 is advanced while the pressure generating piston 509 is simultaneously retreated by the respective motors 556, 549 under control of the electronic control system to compensate the volume transfer of liquid 2 from the liquid supply container 553 to the liquid container portion 560 in the propulsion device. The displacement of the pistons may be precisely controlled to accurately determine the volume of liquid to be filled in the container portion 560, and therefore to be injected.

Once the filling operation is completed, the valve is switched to the closed position blocking the container portion outlet 561 and the liquid supply conduit 552 as shown in FIG. 5b. The pressure generating mechanism can then be operated to compress the compressible substance 7, which is advantageously a liquid polysiloxane, thereby also putting the liquid to be injected 2 under pressure within the container 504. The 'armed' injection device can then be actuated, by pressing an 'inject' button or by any other command signal, that instructs the valve actuator 562 to switch rapidly from the closed position to the actuated position, as shown in FIG. 5c, to propel the liquid through the nozzle orifice. The armed injection device can also be disarmed, for example in case the dosage needs to be corrected, or for any other reason, by simply reversing the aforementioned operations.

It may be noted that the electronic control system could also be connected to a wireless and/or land-based telecommunications network such that information can be received from and/or sent to a remote server. This would enable for example the time of injection and the dosage to be surveyed or even controlled remotely, whether automatically or under the surveillance of a medical practitioner. The electronic control system could also keep a log of the injections (their dosage and times) for control and information purposes.

The propulsion units described herein have applications other than transdermal injection of liquids in the medical or cosmetic field, for example for piercing ears or other tissue. More generally, the propulsion units described herein may be used for the propulsion of any liquid, such as paint or ink, or could be used to propel a solid, for example driven by the piston 10, 210.

The invention claimed is:

1. An injection device having a propulsion system comprising a container, a re-usable pressure generating mechanism and a primary source of potential energy for propelling a fluid with sufficient pressure through an orifice to create a jet enabling subcutaneous or intracutaneous delivery of the fluid, the source of potential energy comprising a compressible substance put under pressure within the container by the pressure generating mechanism, whereby said potential energy is substantially a compression energy of said substance, and further comprising a separating wall in the container enclosing the compressible substance in a rear chamber of the container, the separating wall comprising a valve that can be opened to enable the compressible substance to flow into a front chamber and transmit pressure to said fluid to be injected.

2. The device according to claim 1, wherein the compressible substance has a volumetric compressibility (dV/V) at said pressure within the container greater than 1.2 times the volumetric compressibility of water.

3. The device according to claim 1, wherein the compressible substance is visco-elastic liquid or soft matter.

4. The device according to claim 3, wherein the compressible substance belongs to the family of polysiloxanes.

5. The device according to claim 2, wherein the compressible substance is an elastic solid.

6. The device according to claim 5, wherein the solid is vulcanized silicon rubber.

7. The device according claim 1, wherein the volume of compressible substance is reduced by displacing a piston of the pressure generating mechanism.

8. The device according to claim 1, wherein the liquid to be injected is received in a single-use capsule or ampoule insertable into the container of the propulsion system which forms a unit.

9. The device according to claim 8, wherein the compressible substance is permanently mounted in the container.

10. The device according to claim 8, wherein the compressible substance is mounted in the capsule.

11. The device according to claim 8, wherein said container comprises a separable portion, such as a cap, to open the container portion and enable the ampoule or capsule to be mounted therein.

12. The device according to claim 1, further comprising retaining means comprising a plug for maintaining the pressure of the compressible substance in the container prior to use by closing an orifice or a passage.

13. The device according to claim 12, wherein the plug is mechanical plug that may be displaced to liberate said passage or orifice.

14. The device according to claim 8, wherein the ampoule comprises a flexible or deformable wall fixed to the nozzle portion to contain the fluid to be injected therein.

15. The device according to claim 14, wherein a plug is arranged in the nozzle portion.

16. An injection device having a propulsion system comprising a container, a re-usable pressure generating mechanism and a primary source of potential energy for propelling a fluid with sufficient pressure through an orifice to create a jet enabling subcutaneous or intracutaneous delivery of the fluid, the source of potential energy comprising a compressible substance put under pressure within the container by the pressure generating mechanism, whereby said potential energy is substantially a compression energy of said substance, wherein the liquid to be injected is received in a single-use capsule or ampoule insertable into the container of the propulsion system which forms a unit, the ampoule comprising a flexible or deformable wall fixed to the nozzle portion to contain the fluid to be injected therein, a plug is arranged in the nozzle portion, wherein the plug is made of high tensile strength wire.

17. An injection device having a propulsion system comprising a container, a re-usable pressure generating mechanism and a primary source of potential energy for propelling a fluid with sufficient pressure through an orifice to create a jet enabling subcutaneous or intracutaneous delivery of the fluid, the source of potential energy comprising a compressible substance put under pressure within the container by the pressure generating mechanism, whereby said potential energy is substantially a compression energy of said substance, the injection device further comprising a liquid supply system having a liquid supply reservoir interconnectable with the propulsion system.

18. An injection device having a propulsion system comprising a container, a re-usable pressure generating mechanism and a primary source of potential energy for propelling a fluid with sufficient pressure through an orifice to create a jet enabling subcutaneous or intracutaneous delivery of the fluid, the source of potential energy comprising a compressible substance put under pressure within the container by the pressure generating mechanism, whereby said potential energy is substantially a compression energy of said substance, and further comprising a liquid supply reservoir wherein the liquid supply reservoir is interconnectable with the propulsion system through a valve controlling the blocking an opening of the nozzle orifice.

19. The device according to claim 18, wherein the valve comprises a cylindrical portion comprising a first passage therein for interconnecting the liquid supply container with the propulsion system in a refiling position of the valve, and a second passage for interconnecting the propulsion system with the nozzle orifice in an actuated position of the valve.

20. The device according to claim 17, wherein the liquid supply system comprises a feed mechanism for dosing the supply of the liquid, the feed mechanism and the pressure generating mechanism being driven by motors controlled by an electronic control system.

21. An injection device having a propulsion system comprising a container, a re-usable pressure generating mechanism, a primary source of potential energy for propelling a fluid with sufficient pressure through an orifice to create a jet enabling subcutaneous or intracutaneous delivery of the fluid, the source of potential energy comprising a compressible substance put under pressure within the container by the pressure generating mechanism, whereby said potential energy is substantially a compression energy of said substance, and a secondary source of potential energy generating a lower pressure than the primary source of potential energy.

22. The device according to claim 21, wherein the secondary source of potential energy comprises a spring.

23. The device according to the claim 21 wherein the secondary source of potential energy comprises a gas in the propulsion system container.

24. An injection device having a propulsion system comprising a container, a re-usable pressure generating mechanism and a primary source of potential energy for propelling a fluid with sufficient pressure through an orifice to create a jet enabling subcutaneous or intracutaneous delivery of the fluid, the source of potential energy comprising a compressible substance put under pressure within the container by the pressure generating mechanism, whereby said potential energy is substantially a compression energy of said substance, the propulsion system further comprising a secondary source of potential energy generating a lower pressure than the primary source of potential energy, wherein the secondary source of potential energy comprises a pair of opposed magnets.

* * * * *